United States Patent [19]

Javitt

[11] 4,427,668

[45] Jan. 24, 1984

[54] 26-HYDROXYCHOLESTEROL AND DERIVATIVES AND ANALOGS THEREOF IN REGULATION OF CHOLESTEROL ACCUMULATION IN BODY TISSUE

[75] Inventor: Norman B. Javitt, New York, N.Y.

[73] Assignee: New York University, New York, N.Y.

[21] Appl. No.: 364,338

[22] Filed: Apr. 1, 1982

[51] Int. Cl.³ .............................................. A61K 31/56
[52] U.S. Cl. ..................................................... 424/238
[58] Field of Search ..................... 260/397.2; 424/236, 424/238

[56] References Cited

PUBLICATIONS

Chem. Abstracts, vol. 95, (1981), Par. 133, 246T.
Chem. Abstracts, vol. 95, (1981), Par. 220215a.

Primary Examiner—Elbert L. Roberts
Attorney, Agent, or Firm—Sughrue, Mion, Zinn, Macpeak & Seas

[57] ABSTRACT

Use of 26-hydroxycholesterol for reducing cholesterol synthesis and/or accumulation in body tissues.

15 Claims, No Drawings

26-HYDROXYCHOLESTEROL AND DERIVATIVES AND ANALOGS THEREOF IN REGULATION OF CHOLESTEROL ACCUMULATION IN BODY TISSUE

BACKGROUND OF THE INVENTION

Cholesterol accumulation in body tissues is recognized as a prime causative factor in a number of diseases. In particular, atherosclerosis is characterized by an abnormal hardening and thickening of the arterial walls brought about by increased deposition and/or generation of fatty materials in the tissues, a principal component of which is usually cholesterol.

Cholesterol is a normal plasma component and also is present in essentially all cell membranes. For cell duplication, the cell must either manufacture more cholesterol or obtain cholesterol from the plasma pool. The cell has receptors which attract and bind cholesterol from the plasma, so that the cholesterol can be transported into the interior of the cell.

Today, it is believed that what is important in managing diseases related to cholesterol metabolism are (1) the rate of cholesterol production and (2) the factors that determine its deposition in blood vessels and other tissues. Of these two aspects, the diseases that occur are primarily related to the amounts deposited in tissues, which in turn is to some extent itself related to production rate and the amount in plasma.

Accordingly, the present invention is concerned with regulating the synthesis distribution and tissue level of body cholesterol. More particularly, the present invention is concerned with reducing abnormally high cholesterol accumulation in body tissues. As discussed hereinbefore, abnormally high cholesterol build-up in the body tissues could be as the result of the cells producing more cholesterol than needed for normal body metabolism and/or as the result of plasma cholesterol depositing in tissues in amounts beyond that needed for metabolic functions.

SUMMARY OF THE INVENTION

It has now been found that 26-hydroxycholesterol level in the body plasma is related to cholesterol accumulation in tissues. More specifically, a reduced level of 26-hydroxycholesterol in the serum is associated with cholesterol build-up in the tissues. Therefore, it is an object of the present invention to provide a process for regulating cholesterol level in the body, particularly of tissue cholesterol, through the monitoring and/or administration of 26-hydroxycholesterol.

Another object of the present invention is to provide a compound which can be administered to humans having cholesterol build-up interiorly along their blood vessels in order to reduce the rate of new cholesterol accumulation.

A further object of this invention is to provide a compound which reduces the rate of cholesterol synthesis by the body.

Still another object of this invention is to provide a means for predicting an individual's predisposition toward tissue cholesterol accumulation. A more specific object of this invention is to provide a means for predicting an individual's predisposition toward atherosclerosis.

Another object of this invention is to provide a process to prevent or at least significantly diminish an individual's future tendency toward accumulation of abnormal levels of cholesterol in the tissues.

Other objects of the invention will be apparent to the skilled artisan from the Detailed Description of the Invention hereinbelow.

Therefore, one aspect of the present invention consists of a process involving the unique property of reducing tissue cholesterol accumulation comprising administering to an individual suffering from abnormally high tissue cholesterol accumulation, a tissue cholesterol rate of accumulation-reducing amount of 26-hydroxycholesterol or a derivative or analog thereof.

Another aspect of the present invention consists of a process for determining an individual's susceptibility toward tissue cholesterol accumulation comprising determining the individual's 26-hydroxycholesterol serum level and comparing that level with standard serum level values.

A further aspect of this invention comprises administering 26-hydroxycholesterol to an individual in an amount sufficient to reduce the rate of cholesterol synthesis.

Still another aspect of this invention is concerned with a process for preventing or significantly reducing potential cholesterol tissue build-up beyond normally acceptable values which comprises monitoring a patient's 26-hydroxycholesterol serum level, comparing that level with the normal range for 26-hydroxycholesterol serum level and when the patient's level is below normal range or toward the lower end of the normal range, say the lower 20 percentile, administering 26-hydroxycholesterol or a derivative or analog thereof to the patient in an amount sufficient to increase the 26-hydroxycholesterol serum level to within the normal range or higher within the normal range. In a preferred embodiment of this aspect of the invention, the monitoring and administration as needed will be carried out periodically over an extended time frame which can be as long as many years.

Other aspects of this invention involve pharmaceutical preparations containing 26-hydroxycholesterol or a derivative or analog thereof in an amount sufficient for use in one or more of the process embodiments of this invention.

In preferred embodiments of this invention, 26-hydroxycholesterol is administered orally or intravenously.

DETAILED DESCRIPTION OF THE INVENTION

As far as is known, the present inventor was first to discover that 26-hydroxycholesterol (cholest-5-ene-3$\beta$,26-diol) is normally present in biological fluids after neonatal life. See Javitt et al, "26-Hydroxycholesterol Identification and Quantitation in Human Serum", *J. Biol. Chem.* 256:12644 (1981).

26-Hydroxycholesterol is present in the serum in free and in esterified form, that is as the alcohol portion of esters formed with naturally-occurring fatty acids such as oleic acid. Theoretically, one mol of 26-hydroxycholesterol can link with two mols of fatty acid. About one-third of the serum 26-hydroxycholesterol is usually present in non-esterified form. The total normal serum concentration of 26-hydroxycholesterol (as free sterol and in esterified form) as measured to date is about 4.3 to 25.6 $\mu$g/100 ml of serum. As a wider cross-section of individuals is studied, it is expected that the normal range will be extended beyond the above range by at least 20%. Accordingly, it is believed that the normal range of 26-hydroxycholesterol in the serum would be about 3 to 31 μg per 100 ml.

As described by Javitt et al in *J. Biol. Chem.* 256:12644 (1981), the concentration of 26-hydroxycholesterol in biological fluids can be determined by GLC-MS analysis, using a known amount of a deuterated analog as a standard. It is expected that more rapid, easier qualitative and quantitative methods for 26-hydroxycholesterol analysis can be developed using standard immunoassay techniques, such as through the use of enzyme substrates, radioactive tracers, etc.

Previous work by others has indicated that 26-hydroxycholesterol present in human atheromata in vivo is of enzymatic origin. Van Lier et al, *Biochemistry* 6, 3269 (1967) and Aringer et al, *Biochim. Biophys. Acta.* 665, 13 (1981). The work of the present inventor is in agreement, but of course prior to the work of the present inventor, the existence of 26-hydroxycholesterol in normal serum throughout life was not known.

It has been known that some oxygenated sterols such as 25-hydroxycholesterol inhibit cholesterol synthesis in vitro. It is known that the rate-limiting enzyme in cholesterol synthesis in vivo is hydroxymethylglutaryl-CoA reductase (hereinafter HMG-CoA reductase), which catalyzes the formation of mevalonic acid from hydroxymethyl glutaric acid. Also, it is believed that regulation of cholesterol synthesis may be through mediation by an oxygenated sterol in the activity of HMG-CoA reductase. See Kandutsch et al, *Science* 201, 498 (1978).

A key factor leading to the present invention was the inventor's discovery that patients with cerebrotendinous xanthomatosis (CTX) have little, if any, 26-hydroxycholesterol in their sera. CTX is characterized by normal cholesterol serum levels but with abnormally high cholesterol accumulation in the tissues. Atherosclerosis is often associated with CTX. $C_{27}$ steroid 26-hydroxylase is absent in the mitochondria of CTX patients, which probably explains the lack of oxidation of cholesterol to 26-hydroxycholesterol in CTX patients. But the lack of 26-hydroxycholesterol appears to be directly related to the increased cholesterol deposition in the CTX patients. It is believed that 26-hydroxycholesterol affects the distribution of cholesterol between the blood serum and the tissues.

The effect of 26-hydroxycholesterol on HMG-CoA reductase activity was determined using the procedures of Chang et al, *J. Biol. Chem.* 256:6304 (1981).

Chinese hamster ovary cells, CHO-K1 cells (also referred to as wild type) were obtained from the American Type Culture Collection and grown in Falcon flasks on Ham's F-12 media containing 10% fetal calf serum. Approximately 2½ days after cells were removed from the stock flask cultures and seeded into petri dishes (60 mm), each containing $0.03 \times 10^6$ cells, they were rinsed with phosphate-buffered saline (PBS) and then grown in F-12 media containing 10% delipidated fetal calf serum for 48 hours with one change of media. Following this, either fresh media (still with delipidated calf serum) or fresh media containing 0.14% DMSO alone or 26-hydroxycholesterol was added and the cells incubated for varying periods of time. Our final concentration of DMSO was less than Chang (0.14% vs. 0.3%) and comparison of HMG-CoA reductase activity at 5 hours with media not containing DMSO gives the same or slightly higher (not significant) values. Under these conditions, over 50% inhibition has been obtained using the 0.25 μM concentration of 26-hydroxycholesterol and incubating for 5 hours. Not only is the mean highly significant but none of the individual control flasks overlap with the individual flasks containing 26-hydroxycholesterol. Using a concentration 10 X greater (2.5 μM) of 25-hydroxycholesterol, Chang reported 80% inhibition at 5 hours.

Table 1 below sets forth average results of this experiment when carried out on a single day. Similar results occurred when the experiment was repeated on other occasions.

TABLE 1

CHINESE HAMSTER OVARY CELL CULTURE

| | HmG-CoA Reductase Activity as Mevalonate Formed | |
|---|---|---|
| Substance Added | HmG Co-A Reductase Activity *(nMol/min/mg protein) | % Inhibition |
| 0.14% DMSO Control | 0.048 | |
| DMSO 0.14% + 26-hydroxycholesterol (0.25 μM) | 0.017 | 65 |

*nanomoles per minute per milligram protein

HMG-CoA reductase activity was determined using the double-label technique of Pitot et al, *J. Lipid Res.* 12:512 (1971) and the thin-layer separation of Shapiro et al, *Anal. Biochem.* 31:383 (1969). Essentially, one adds fluid obtained from the broken cells to a medium containing all the necessary co-factors and after preincubation for 10 minutes, $^{14}$C-HMG-CoA Reductase (New England Nuclear) is added in sufficient concentration to be at zero order kinetics. Usually the specific activity is adjusted so that the final concentration is 87 μM and total counts 90,000 dpm. After 60 min of incubation with shaking at 37° C., $^3$H-mevalonate is added and the incubation terminated by acidification (HCl) which also causes lactonization. The mevalonlactone is separated by thin-layer chromatography and the $^{14}$C/$^3$H ratio determined from which the total amount of $^{14}$C can be calculated (corrected for $^3$H recovered) and expressed per mg of cytosolic protein by the Lowry method.

26-Hydroxycholesterol can be prepared from kryptogenin. See Wachtel et al, *J. Biol. Chem.* 243, 5207 (1968) and Scheer et al, *Am. Chem. Soc.* 78, 4733 (1956). Kryptogenin can be obtained using published procedures from Beth root and from several species of Mexican Dioschorea. Also, kryptogenin is available from Syntex Corporation, Palo Alto, Calif.

As used herein, as a compound to be administered to a patient, 26-hydroxycholesterol includes not only 26-hydroxycholesterol per se but also the mono and diesterified derivatives and other pharmaceutically acceptable derivatives thereof such as the mono and diethers. Most usually, fatty acid, the same or analogous to those naturally occuring, would be used to form the esters, but other inorganic and organic esters, such as the sulfates, carbonates and glucuronides, routinely employed in preparing pharmaceutically acceptable esters could be used. Esterification and/or etherification can occur at the 3- and/or 26- position. Aryl and/or alkyl ethers, such as methyl, ethyl or cycloalheles (i.e. cyclopentyl ethers are contemplated. Furthermore, acid salts and various substituted compounds, for example, those containing elements such as fluorine commonly used in modification of steroid-type compounds, as long as pharmaceutically acceptable, can be used.

By "26-hydroxycholesterol and analogs" as used herein is meant 26-hydroxycholesterol (including the 25R and 25S stereo isomers and mixtures thereof) and related oxygenated sterol compounds, both naturally occurring and synthetically produced, which through study of 26-hydroxycholesterol would be expected to have an analogous cholesterol regulating effect. Some of the useful naturally occurring compounds are believed to be cholest-5-ene 3β, 7α,26-triol, cholest-4-ene-3-one,26-ol, cholestane 3α,26-diol, cholestane 3α, 7α, 26-triol, 3β-hydroxy-cholest-5-enoic acid and 3β-hydroxy-cholen-5-oic acid. Of course, similar to 26-hydroxycholesterol, the various chemical derivatives of these compounds, such as the fatty acid esters and other pharmaceutically acceptable derivatives, where appropriate, could be employed.

The compounds used in the present invention, based on 26-hydroxycholesterol, would be administered in amounts ranging from about 5 mg/kg to 25 mg/kg, one to three times a day.

Administration can be through the use of liquid and solid formulations and also through the use of injectables, such as intravenous injectables, wherein conventional pharmaceutical carriers would be employed.

Suitable pharmaceutical preparations include tablets, capsules, oral liquids and parenteral injectables. Since 26-hydroxycholesterol and the analogs thereof discussed above are solids, tablet and capsule formulations can be employed utilizing conventional diluents, excipients and the like such as lactose in conventional capsule and tablet-making procedures. Parenteral injections could employ solvents conventionally used with lipid-soluble materials, or a salt of the sterol could be prepared which would be soluble in aqueous solvents.

In the aspects of the present invention involving monitoring of a patient's 26-hydroxycholesterol level, the quantitative isotope dilution mass spectrometry method discussed above could be employed. As noted, it is expected that more routine-type immunoassay procedures will be developed.

Variations of the invention will be apparent to the skilled artisan.

What is claimed is:

1. A process for reducing the rate of cholesterol synthesis by a human which comprises administering to said human a cholesterol synthesis rate-reducing amount of 26-hydroxycholesterol or a fatty acid ester, a sulfate, a carbonate of a glucuronide thereof.

2. A process for reducing the rate of cholesterol accumulation in body tissues which comprises administering to an individual 26-hydroxycholesterol or a fatty acid ester, a sulfate, a carbonate or a glucuronide thereof, in an amount sufficient to reduce the rate of cholesterol accumulation in the body tissues of said individual.

3. A process for treating atherosclerosis which comprises administering to an individual having atherosclerosis 26-hydroxycholesterol or a fatty acid ester, a sulfate, a carbonate or a glucuronide thereof, in an amount sufficient to reduce the rate of cholesterol accumulation along the arteries of said individual.

4. A process for preventing abnormally high cholesterol accumulation in body tissues which comprises determining the level of 26-hydroxycholesterol in the serum or other biological fluid of an individual, comparing that level with the normal range for 26-hydroxycholesterol in serum or other biological fluid and then administering 26-hydroxycholesterol or a fatty acid ester, a sulfate, a carbonate or a glucuronide thereof to said individual in an amount sufficient to raise the 26-hydroxycholesterol level of said individual to at least within said normal range.

5. The process of claim 4 wherein the level of 26-hydroxycholesterol is determined in blood serum.

6. The process of any of claims 1 to 5 wherein 26-hydroxycholesterol or a fatty acid ester thereof is administered.

7. The process of claim 6 wherein the 26-hydroxycholesterol is administered in an amount of about 5 to 25 mg/kg.

8. The process of claim 6 wherien the ester is a sulfate.

9. The process of claim 1 wherein the 26-hydroxycholesterol or fatty acid ester, sulfate, carbonate or glucuronide thereof is administered in an amount, based on 26-hydroxycholesterol, of about 5 to 25 mg/kg.

10. The process of claim 2 wherein the 26-hydroxycholesterol or fatty acid ester, sulfate, carbonate or glucuronide thereof is administered in an amount, based on 26-hydroxycholesterol, of about 5 to 25 mg/kg.

11. The process of claim 3 wherein the 26-hydroxycholesterol or fatty acid ester, sulfate, carbonate or glucuronide thereof is administered in an amount, based on 26-hydroxycholesterol, of about 5 to 25 mg/kg.

12. The process of claim 4 wherein the 26-hydroxycholesterol or fatty acid ester, sulfate, carbonate or glucuronide thereof is administered in an amount, based on 26-hydroxycholesterol, of about 5 to 25 mg/kg.

13. The process of claim 5 wherein the 26-hydroxycholesterol or fatty acid ester, sulfate, carbonate or glucuronide thereof is administered in an amount, based on 26-hydroxycholesterol, of about 5 to 25 mg/kg.

14. A method for predicting an individual's predisposition toward tissue cholesterol accumulation which comprises determining the level of 26-hydroxycholesterol in the serum or other biological fluid of said individual and comparing that level with the normal range for 26-hydroxycholesterol in serum or other biological fluid.

15. The process of claim 14 wherein the level of 26-hydroxycholesterol is determined in blood serum.

* * * * *